United States Patent [19]

Goulianos et al.

[11] 4,311,908
[45] Jan. 19, 1982

[54] SIMPLE ELECTRONIC APPARATUS FOR THE ANALYSIS OF RADIOACTIVELY LABELED GEL ELECTROPHORETOGRAMS

[75] Inventors: Konstantin Goulianos; Karen K. Smith; Sebastian N. White, all of New York, N.Y.

[73] Assignee: The Rockefeller University, New York, N.Y.

[21] Appl. No.: 127,042

[22] Filed: Mar. 4, 1980

[51] Int. Cl.$^3$ .............................................. G01T 1/18
[52] U.S. Cl. .................................... 250/374; 250/388
[58] Field of Search ............... 250/374, 375, 382, 384, 250/385, 388, 389

[56] References Cited

U.S. PATENT DOCUMENTS

| | | | |
|---|---|---|---|
| 3,483,377 | 12/1969 | Borkowski et al. | 250/374 |
| 3,517,194 | 6/1970 | Borkowski et al. | 250/385 |
| 3,772,521 | 11/1973 | Perez-Mendez | 250/385 |
| 3,898,465 | 8/1975 | Zaklad et al. | 250/385 |
| 3,911,279 | 10/1975 | Gilland et al. | 250/385 |
| 3,975,638 | 8/1976 | Grunberg et al. | 250/385 |
| 3,975,639 | 8/1976 | Allemand | 250/385 |
| 4,075,492 | 2/1978 | Boyd et al. | 250/385 |
| 4,149,109 | 4/1979 | Kreutz et al. | 250/382 |
| 4,150,290 | 4/1979 | Erskine et al. | 250/385 |

OTHER PUBLICATIONS

Breskin et al., Two-Dimensional Drift Chambers, Nuclear Instruments and Methods, vol. 119, 1974, pp. 1-5.
Bouchier et al., Investigation of Some Properties of Multiwire Proportional Chambers, European Organization for Nuclear Research, Jun. 1970, pp. 1-19.
Flat Helical Delay Lines for Position Readout Along the Anode Wire in NWPC and Drift Chambers, Akuno et al., IEEE Trans., vol. NS-24, No. 1, 2/77.
Laskey et al., Quantitative Film Detection of $^3$H and $^{14}$C in Polyacrylamide Gels by Fluorography, Eur. Biochem., vol. 56, 1975, pp. 335-341.
Radeka, Signal, Noise and Resolution in Position-Sensitive Detectors, Nuclear Science Symposium, San Francisco, Nov. 14-16, 1973.
Gabriel et al., Autoradiography with a Position Sensitive Counter, North-Holland Publish. Co., Amsterdam, vol. 39, No. 3, 1974, pp. 307-309.

*Primary Examiner*—Davis L. Willis
*Attorney, Agent, or Firm*—Oblon, Fisher, Spivak, McClelland & Maier

[57] ABSTRACT

A high resolution position sensitive radiation detector for analyzing radiation emanating from a source, constructed of a thin plate having an elongated slot with conductive edges acting as a cathode, a charged anode wire positioned within 0.5 mm adjacent the source and running parallel to the slot and centered therein, an ionizable gas ionized by radiation emanating from the source provided surrounding the anode wire in the slot, a helical wire induction coil serving as a delay line and positioned beneath the anode wire for detecting gas ionization and for producing resulting ionization signals, and processing circuits coupled to the induction coil for receiving ionization signals induced therein after determining therefrom the location along the anode wire of any radiation emanating from the source. An ionization gas of 70% Ar, 29% Isobutane, 0.6% Freon 13BI, and 0.4% Methylal is used.

9 Claims, 11 Drawing Figures

SIMPLE ELECTRONIC APPARATUS FOR THE ANALYSIS OF RADIOACTIVELY LABELED GEL ELECTROPHORETOGRAMS

The present invention was wholly or partially made with funds provided the Department of Energy. Accordingly, the U.S. Government has a royalty free license under any patent granted with respect to this invention.

BACKGROUND OF THE INVENTION

1. Field of the Invention

This invention relates to a high resolution position sensitive radiation detector system, as for example may find extensive but not exclusive utilization in gel electrophoresis.

2. Description of the Prior Art

Experiments in biology often involve the analysis of distributions of radioactively labeled molecules. Such distributions are obtained, for example, in gel electrophoresis when a mixture of electrically charged molecules (proteins, RNA, DNA) migrates through a thin layer of viscous medium (gel) under the influence of an electric field. According to their mobilities, different types of molecules migrate to different positions in the gel forming distinct bands. Two aspects of the information contained in an "electrophoretogram" are of interest: (a) the location of the bands which identifies the molecules and (b) the number of radioactive molecules in each band.

Electrophoretograms are generally analyzed for this information either by slicing the original gel and dissolving the individual pieces in a flour for scintillation counting, or by exposing the gel to a photographic emulsion (autoradiography). Gel slicing yields quantitative results but the resolution in the position of the bands is limited by the size of the slice which is usually 1 mm. Autoradiography offers excellent position resolution (typically $\pm 0.2$ mm, limited by the thickness of the sample and of the film) but does not yield a direct quantitative measurement of the relative intensity of different bands. Both methods of analysis require several hours to several days.

An apparatus for autoradiography with a position sensitive counter has been reported previously by Gabriel et al., FEBS Letters 39, 307 (1974). Position localization in that apparatus was accomplished by determining the difference in rise time of the signals arriving at the two ends of a resistive anode wire. The spatial resolution achieved was 3 mm. In the past few years, methods for determining the avalanche position along the anode wire of a proportional counter have received considerable attention. Also, the technique of avalanche localization through the induced pulse on a delay line, on which the present invention is based, has been developed for use in high energy physics experiments, as reported by Breskin et al., Nuclear Instr. and Methods 119, 1 (1974), and Okuno et al. IEEE Trans. Nucl. Sci., NS-24, 213 (1977).

Additional disclosures relating to position-sensitive radiation detectors can be found in the patent literature as represented by U.S. Pat. No. 3,483,377 to Borkowski et al., U.S. Pat. No. 3,517,194 to Borkowski et al., and U.S. Pat. No. 4,149,109 to Kreutz et al. The two Borkowski et al. patents disclose a position-senstitive detector formed of an ionizing radiation detecting element having a very high resistance collector which is of sufficient resistance per unit length to provide a voltage pulse at an output end thereof, wherein the rise time of the voltage pulse is proportional to the distance between the location of an ionizing event and the end of the collector. A low resistance reference electrode is placed in proximity to the high resistance collector electrode such that an ionizing event additionally produces a constant rise time reference pulse independent of impact position in the reference electrode. Then, by time comparison of the position independent reference pulse with the position dependent pulse produced in the high resistance collector electrode, Borkowski et al. determine radiation impact position.

In the above-noted Kreutz et al. patent, a location-sensitive proportional counter tube is provided with a trough-shaped cathode in a counting chamber in which is longitudinally extended a resiliently elastic anode wire. Fasteners engage the end of the anode wire to mount the anode wire equidistantly from the side walls of the cathode trough and are connected in electrical connection with the input resistor of a preamplifier. The counting chamber is pressurized by means of inlet and outlet apertures with a pressurized counter tube gas, for example, 90% argon, 10% methane.

In addition to the above references, further methods and apparata for radiation localization are disclosed in U.S. Pat. Nos. 3,772,521; 3,898,465; 3,975,638; 3,975,639; 4,075,492; and 4,150,290.

SUMMARY OF THE INVENTION

Accordingly, one object of this invention is to provide a new and improved position sensitive radiation detector which exhibits improved resolution in determining the positional location of incident radiation.

Another object of this invention is to provide a system of the above-noted type capable of yielding quantitative as well as qualitative measurement of the position and intensity of radiation emanating from an electrophoretic gel.

Yet another object of this invention is to provide a new and improved system for fast quantitative analysis of electrophoretograms which is capable of counting individually all the $\beta$-particles emerging from the surface of the gel and locating each particle to within $\pm 0.5$ mm as it emerges from the gel.

A further object of this invention is to provide a novel high resolution position sensitive radiation detector capable of high speed position location and quantization of incident radiation.

Another object of this invention is to provide a system of the above-noted type which is simple to construct and operate using readily available electronic components.

These and other objects are achieved according to the invention by providing a high resolution position sensitive radiation detector for analyzing radiation emanating from a source, constructed of a thin plate having an elongated slot with conductive edges acting as a cathode, a charged anode wire positioned adjacent the source and running parallel to the slot and centered therein, an ionizable gas surrounding the anode wire in the slot such that the gas is ionized by radiation emanating from the source into the gas, induction means for detecting ionization produced in the gas by incident radiation and for producing resulting ionization signals, and processing means coupled to the induction means for receiving ionization signals induced therein by ionization of the gas due to radiation emanating from the source and for determining from the ionization signals the location along the anode wire of radiation emanating from the source.

In a preferred embodiment, the induction means is formed of a helical wire coil positioned adjacent the anode wire opposite the source and having an axis parallel to the anode wire. Additionally, in the preferred embodiment, an ionization gas consisting of 70% Ar, 29% Isobutene, 0.6% Freon 13B1, 0.4% methylal is used.

The geometry of the system according to the invention permits a measurement uncertainity which is comparable to that of photographic emulsions, but which is limited only by the geometry and more particularly the spacing of the charged anode wire from the radiation source and the disposition of this wire within the slot formed on the cathode plate. Optimally, a 0.5 mm distance is provided between the anode wire and the radiation source in order to achieve the improved resolution performance of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
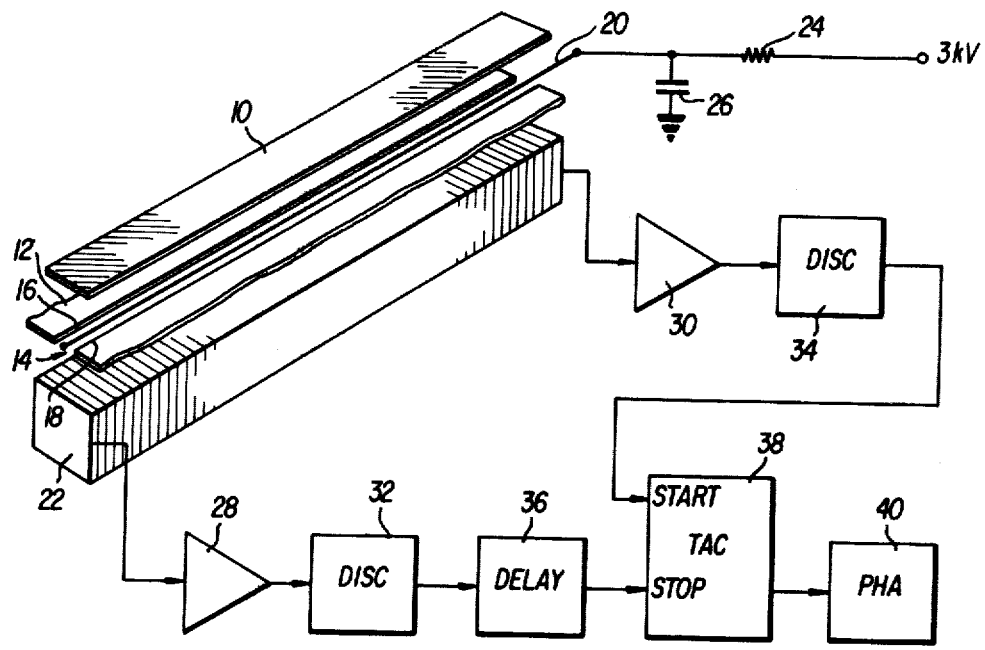
FIG. 1 is a schematic partially in perspective drawing of the apparatus of the invention including associated electronics.

Referring now to the drawings, wherein like reference numerals designate identical or corresponding parts throughout the several views, and more particular to FIG. 1 thereof, the system of the invention which is designed to be used in conjunction with a source 10 of radiation, such as an electrophoretogram, is seen to include a thin plate 12 having an elongated slot 14 and provided with conductive edges 16 and 18 on either side of the slot 14, which edges 16 and 18 serve as a cathode. Positioned between the edges 16 and 18 is an anode wire 20 running parallel to the slot 14 and centered therein. Positioned below the anode wire 20 is in ionization detector implemented by means of a helical wire coil 22 positioned below the plate 12 and having an axis parallel to the axis of the anode wire. Although not shown in FIG. 1, the system of the invention further includes an ionizable gas surrounding the anode wire 20 at least in the region surrounding the anode wire 20 in the slot 14 between the conductive edges 16 and 18 thereof.

The anode wire 20 is maintained at a high voltage, for example 3 kv through a filter circuit formed of resistor 24, typically 30 M ohms and filtering capacitor 26. As also shown in FIG. 1, opposite ends of the helical coil 22 are coupled to respective amplifiers 28 and 30 the outputs of which are coupled to respective voltage threshold discriminator circuits 32 and 34. The output of discriminator 32 is coupled to a delay line 36 having an output serving as a STOP input to a time to amplitude converter (TAC) 38. On the other hand, the output of discriminator circuit 34 is coupled to the START input of TAC 38. TAC 38 produces an output coupled to a pulse height analyzer circuit 40. Amplifiers 28 and 30, discriminator circuits 32 and 34, delay circuit 36, TAC 38, and pulse height analyzer 40 are of conventional design as is well known to those skilled in the art, and accordingly for the sake of brevity the detailed description thereof and accompanying disclosure is omitted.

The principal of operation of the system shown in FIG. 1, which employs a position sensitive single-wire gas proportional counter, is nextly described. The radiation source 10, such as an electrophoretogram, is placed on top of the slot 14, which is typically 20 cm long by 6 mm wide, approximately 0.5 mm away from the charged anode wire 20, which may be a fine gold-plated tungsten wire. The helical ionization detecting coil 22 is located directly below the anode wire 20 approximately 2 mm away from the anode wire 20.

Figure 2:
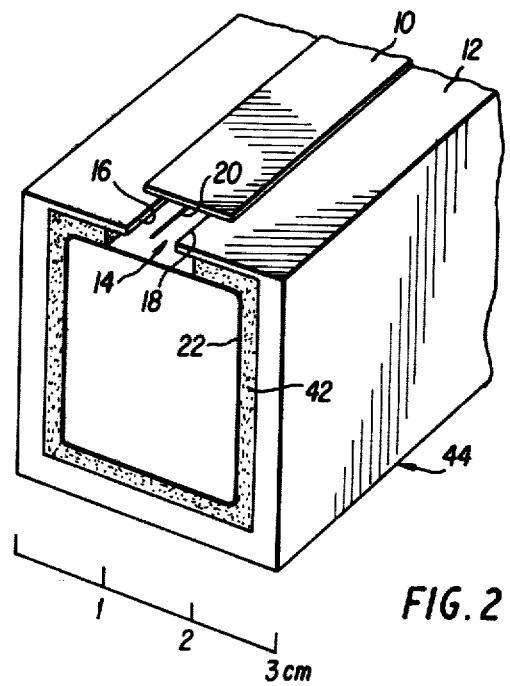
FIG. 2 is a fragmentary perspective view partially in cross section of the apparatus of the invention.

FIG. 2 shows a practical implementation of the system of the invention in which the ionization detection coil 22 is disposed within a dielectric 42 encased in a square aluminum pipe 44. One of the four 3 mm thick walls of the square aluminum pipe which houses the ionization detecting coil is machined down to a 1 mm thickness, with a 6 mm wide slot 14 opened along the length of the aluminum pipe 46. The machined wall of the aluminum pipe 44 then serves as the plate 12 shown in FIG. 1 and is so labeled in FIG. 2, it being understood that the edges 16 and 18 of the slot 14 shown in FIG. 2 serve as the cathode of the system of the invention shown in FIG. 2. As further shown in FIG. 2, a gold-plated tungsten anode wire of 0.020 mm diameter was stretched along the center of the slot 14, approximately 0.5 mm below the outer surface of the slot 14 and 2 mm above the ionization detection coil 22. The radiation detecting portion of the system of the invention, as shown in FIG. 2, may be enclosed in a sealed chamber containing the porportional counter gas atmosphere noted above, or otherwise other measures may be taken to assure that the requisite porportional counter gas atmosphere is provided in the vicinity of the anode wire 20 between the slot 14 of the plate 12. As also shown in FIG. 2, the radiation source 10, or sample to be measured, is placed on top of the slot 14.

During operation, $\beta$-particles emitted from the source 10, typically an electrophoretic gel, ionize the gas along their trajectories. The ionization electrons move along the electric field lines towards the anode wire 20 and into the high field region immediately surrounding the wire 20 where they undergo avalanche multiplication. As the avalanche separates into electrons collected by the anode wire 20 and a positive ion cloud moving away, a positive signal is induced on the ionization detection coil 22, serving as a delay line, at the position of the avalanche. This signal propagates towards the two ends of the coil 22 with a velocity determined by the physical characteristics of the line. A measurement of the difference in time of arrival of the signals at the two ends of the delay line coil 22 yields the position of the avalanche along the anode wire 20 and hence the position of the $\beta$-particle in its closest approach to the wire 20. This position is within ±0.5 mm (distance of sample from wire) from the actual position of the $\beta$-particle as it emerges from the surface of the gel. The geometry is such that an entire band is projected onto the same position along the anode wire within the above mentioned limitation.

In order to reduce the geometrical error in determining the point at which the $\beta$-particle emerges from the gel source 10, one must reduce the distance from the gel 10 to the anode wire 20. However, this requires that the measurement be derived from the ionization deposited in a correspondingly short distance along the track. For a given amplification, the shorter the track length sampled, the smaller the signal induced on the delay line. Since the error due to electronics is inversely proportional to the signal-to-noise ratio, reducing the distance from the gel source 10 to the wire 20 broadens the electronic resolution. Furthermore, since the ionization deposited in a given track length decreases as the energy of the $\beta$-particle increases, the electronic resolution in a counter operated in proportional mode is not constant over the energy spectrum of the $\beta$-particles. These problems can be overcome by using an ionization gas mixture known among high energy physicists as "magic" gas (70% Ar, 29% Isobutane, 0.6% Freon 13B1, 0.4% Methylal). With this gas mixture the number of ion pairs created in an avalanche can be an order of magnitude larger than obtainable with standard proportional counter gas mixtures. At high enough anode voltage the avalanche becomes limited so that the signal does not depend strongly on the amount of ionization initiating the avalanche. This saturation effect leads to uniform resolution over the entire energy spectrum of the $\beta$-particles. Owing to the large avalanche size, an electronic resolution as narrow as ±0.3 mm can be achieved, which is small compared (in quadrature) to the geometric resolution of ±0.5 mm.

Figure 3A:
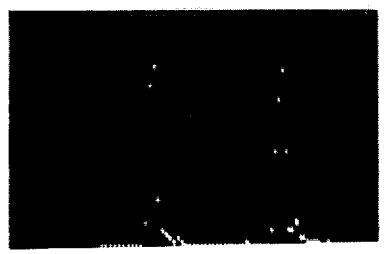
FIG. 3a is a display of the results obtained by the apparatus of the invention for two bands separated by 1 centimeter, obtained with an X-ray radiation source.
Figure 3B:
FIG. 3b is a display of the results provided by the apparatus of the invention for two bands separated by 1 centimeter, obtained with a $\beta$-source.

The results presented in FIGS. 3a, 3b have been obtained with an apparatus dimensioned as shown in FIG. 1. The delay line is constructed as follows:

| DELAY LINE | |
|---|---|
| Length | 20 cm |
| Cross Section | 22 mm × 22 mm, nylon core |
| Wire | 0.2 mm in diameter, "magnet" wire |
| Pitch | 50 turns/cm |
| Dielectric (42) | Phenolic G-10, 1.5 mm thick |
| Ground | 25 mm × 25 mm × 3 mm thick square aluminum pipe |
| Delay | 2.5 nsec/mm (in each direction) |
| Impedance | 1700 $\Omega$ |

With "magic" gas in the slot 14, the anode wire 20 is coupled to +3 kV. In order to ensure electrical isolation between anode wire 20 and coil 22, the coil 22 is insulated from the anode wire with a 0.1 mm thick plastic sheet e.g., as sold under the trademark Mylar ™ by E. I. du Pont de Nemours and Co. (not shown).

Each of the two ends of the ionization induction coil 22 are connected through a 1700 $\Omega$ resistor (equal to the characteristic impedence of the line) to respective amplifiers 32, 34. The amplifier signals, after discrimination and appropriate delay, are used to start and stop the Time to Amplitude Converter (TAC) 38. (Delay line 36, having a delay equal to the maximum signal delay through the coil, is inserted in order to assure that induced ionization signals cannot be applied to TAC 38 in an incorrect order.) The output of the TAC 38 is fed into the Pulse Height Analyzer (PHA) 40, as previously described. The resulting time spectra are either displayed on a PHA scope or transferred via an interface to a computer and displayed using computer graphics. In the latter case the measured distribution is available on a computer data base which can be of some advantage in analyzing these distributions.

The resolution of the apparatus was measured using two different types of radioactive sources: an x-ray source ($^{55}$Fe, 5.9 keV x-rays) and a $\beta$-source ($^{14}$C, 158 keV $\beta-$). The use of the two sources enabled the determination of the individual contributions to the overall resolution of the electronics and of the geometry. The x-ray source illuminated the chamber through a 0.25 mm wide, 1.5 mm thick aluminum collimator placed perpendicular to the anode wire. Interactions in the gas of this collimated band of x-rays result in avalanches whose position distribution along the wire has a full width of 0.25 mm (the width of the collimator slot). Any broadening of the measured distribution was attributed to the electronics. The $\beta$-source was formed by "painting" thin lines of a $^{14}$C-labeled solution on a piece of paper simulating the bands of an electrophoretogram. The width of the lines was determined by film autoradiography. Because the $\beta$-particles are emitted isotropically, one expects a geometric broadening of these lines (parallax effect) in addition to the electronic broadening discussed above.

Figure 3C:
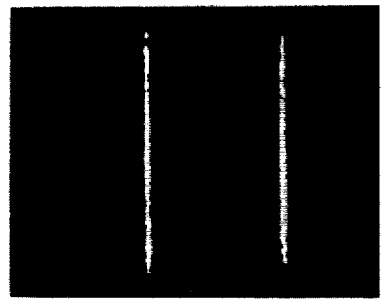
FIG. 3c is a film auto radiography of the $\beta$-source.

FIGS. 3a, 3b and 3c displays the results for two bands separated by 1 cm, obtained with (a) the x-ray source, (b) the $\beta$-source and (c) film autoradiography of the $\beta$-source, respectively. The full width at half maximum (FWHM) of the x-ray bands, FIG. 3a is 0.7 mm (the average width of the two peaks is 2.5 channels at 35 channels/cm). Subtracting the slot width is quadrature, a 0.6 mm FWHM electronic resolution is obtained. The $\beta$-source bands, FIG. 3b, have a FWHM of 1.4 mm. However, the width of the painted radioactive lines themselves is 0.5 mm as evidenced by the film autoradiogram, FIG. 3c. Thus, the detector resolution is ±0.6 mm half width at half maximum, consistent with the errors due to the geometry and the electronics.

Figure 5A:
FIGS. 5a and 5b are respective comparison views of a film autoradiogram of a $^{14}$C-labeled gel with an electroradiogram of the same gel obtained by the system of the invention.
Figure 5B:
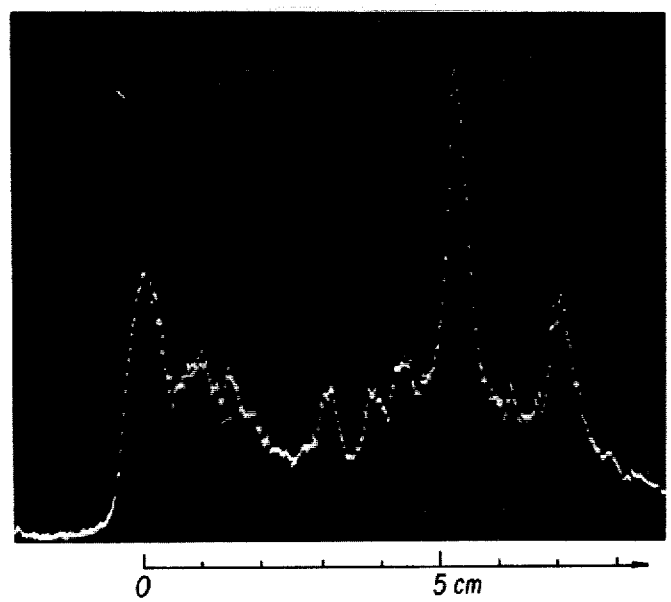
Figure 4A:
FIGS. 4a and 4b are respectively radiograms of a sample $^{14}$C-labeled gel obtained by film autoradiography and by means of a system of the invention.
Figure 4B:
Figure 6A:
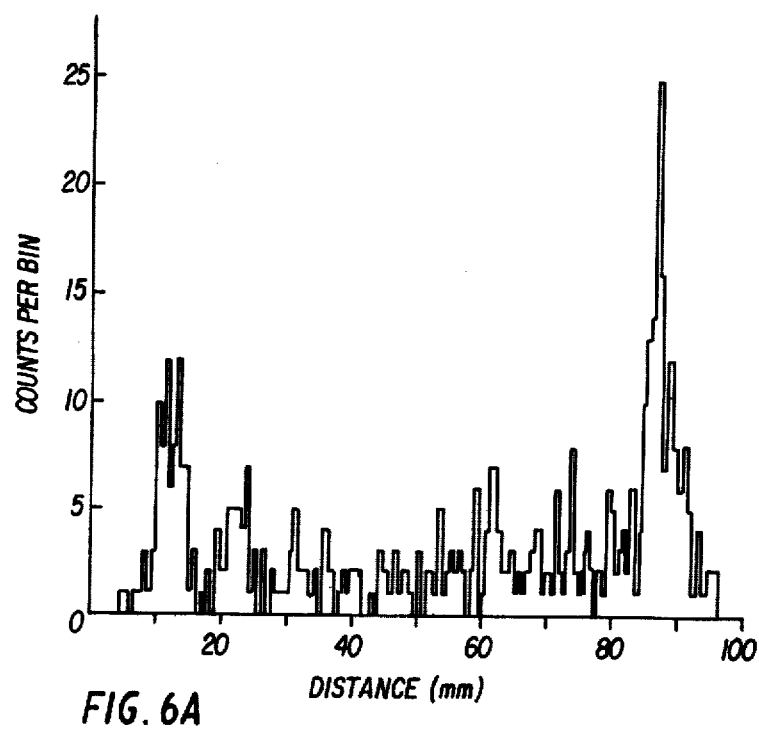
FIGS. 6a and 6b are respective graphs of radiograms of a 20,000 dpm $^3$H-gel obtained in a 10 minute run using the system of the invention versus a radiogram obtained by conventional gel slicing and scintillation counting.
Figure 6B:
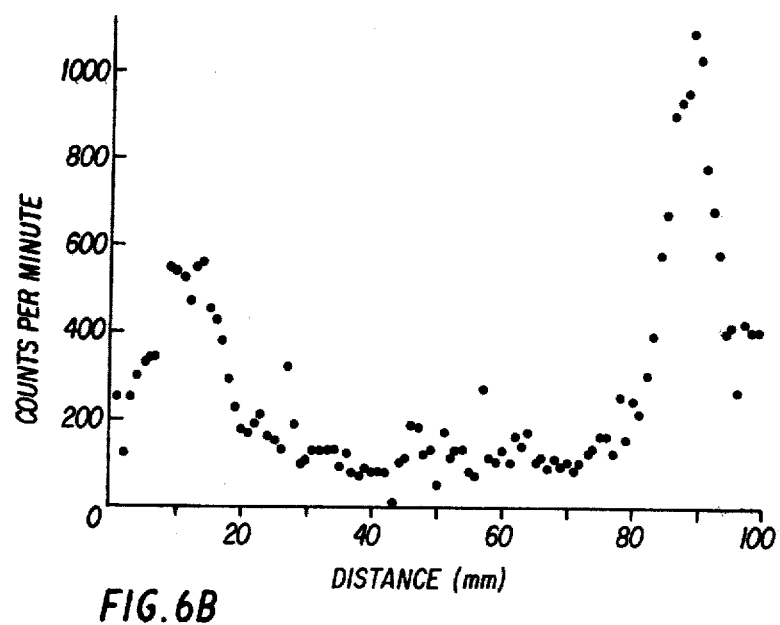

In FIGS. 4a and 5a are shown film autroradiograms of two actual $^{14}$C-gels, 5,000 dpm and 25,000 dpm respectively, compared to FIGS. 4b and 5b which show results obtained using the system of the invention (electroradiograms). The gels, which were 7–13% polyacrylamide gradient slab gels dried onto Whatman filter paper, were exposed to film for two weeks. The electroradiograms in FIGS. 4a, 4b and 5a, 5b were accumulated over a 20 minute period and in an overnight run, respectively. In FIGS. 6a and 6b are compared radiograms of a $^3$H-gel obtained by the standard gel slicing technique and by the system of the invention.

For the analysis of gels labeled with $^{14}$C, or other $\beta$-emitters with energy greater than $^{14}$C (i.e., $^{35}$S, $^{32}$P, but not $^3$H), an enclosed chamber has been used in which the aluminum slit was covered with a thin plastic window, e.g., as sold under the trademark Mylar ™ by E. I. du Pont de Nemours and Co. This simplifies the use of the system and permits the analysis of hydrated gels.

The response of the detector of the invention to $^{125}$I (27 keV x-rays) has also been studied and the same electronic resolution as with $^{55}$Fe has been obtained. Unlike $\beta$-particles, x-rays do not ionize the gas along their trajectories unless they are absorbed by an atom, thereby releasing an electron. The absorption length for 27 keV x-rays in "magic" gas is about 100 cm. This affects the analysis of $^{125}$I-labeled gels using the system of the invention in two ways. Firstly, about 400 times higher activity is now needed in order to obtain the same counting rate as with $^{14}$C-gels. Secondly, since the geometric resolution is now determined by the total thickness of the gas layer below the gel, this layer must be restricted to 1 mm thickness if the same resolution as with $\beta$-emitters is desired. This can be accomplished by placing plastic windows on either side of the aluminum slit, e.g., as sold under the trademark Mylar ™ by E. I. du Pont de Nemours and Co.

Recapitulating, the system of the invention is capable of performing automatic quantitative analysis of electrophoretograms with a resolution of $\pm 0.6$ mm. The counting rate from a standard 25,000 dpm $^{14}$C-labeled electrophoretogram is about 20/sec. For $^{3}$H-labeled samples, the counting rate is about 10 times smaller. Thus, in relatively short periods of time, radiograms can be obtained which combine the quantitative feature of the gel slicing technique with the good resolution of film autoradiography.

The improved performance of the system of the invention is directly attributable to the geometry defined by the slot 14 with associated edges 16 and 18, anode wire 20, and ionization detection coil 22, as well as the surrounding of the anode wire 20 with an appropriate ionization gas, as noted above. Thus, the anode wire is optimally disposed approximately 0.5 mm away from the source. In that regard, improved performance can be realized according to the system of the invention by providing a cathode plate having a $1.0\pm 0.5$ mm thickness including a cathode plate slot having a width of $6.0\pm 2.0$ mm, with an anode wire 20 positioned less than $1.0\pm 0.5$ mm below the source 10, and the helical ionization detection coil 22 positioned below the anode wire 20.

Obviously, numerous modifications and variations of the present invention are possible in light of the above teachings. For example, by pressurizing the ionization gas within the slot 14 of the invention, it is expected that ionization of the ionization gas particles emanating from the source 10 will be enhanced such that it may be possible to further improve the resolution offered by the system of the invention. It is therefore to be understood that within the scope of the appended claims, the invention may be practiced otherwise than as specifically described herein.

What is claimed as new and desired to be secured by Letters Patent of the United States is:

1. A high resolution position sensitive radiation detector for analyzing radiation emanating from a source, comprising:
   a plate having an elongated slot with conductive edges acting as a cathode;
   a charged anode wire positioned adjacent said source and running parallel to said slot and centered within said slot in said plate;
   an ionizable gas surrounding said anode wire in said slot said gas ionized by radiation emanating from said source into said gas;
   induction means for detecting ionization produced in said gas by said radiation and for producing resulting ionization signals; and
   processing means coupled to said induction means for receiving ionization signals induced therein and for determining from said ionization signals the location along said anode wire of radiation emanating from said source.

2. A system according to claim 1, wherein said induction means comprises:
   a helical wire coil positioned adjacent said anode wire opposite said source and having an axis parallel to said anode wire, said coil having opposed ends for making electrical connection thereto.

3. A system according to claim 1, further comprising:
   said anode wire disposed less than 1.0 mm away from said source.

4. A system according to claim 3, further comprising:
   said anode wire disposed approximately 0.5 mm away from said source.

5. A system according to claim 2, further comprising:
   said helical coil positioned within at least 2.0 mm from said anode wire.

6. A system according to claim 2, further comprising:
   said cathode plate having a $1.0\pm 0.5$ mm thickness;
   said cathode plate slot having a width of $6.0\pm 2.0$ mm;
   said anode wire positioned less than $1.0\pm 0.5$ mm below said source; and
   said helical coil positioned below said anode wire.

7. A system according to claim 6, further comprising:
   said cathode plate having a thickness less than 3.0 mm.

8. A system according to claim 2, wherein said processing means comprises:
   first and second amplifiers connected to respective ends of said helical coil;
   first and second threshold level discriminators coupled to said first and second amplifiers, respectively;
   delay line means coupled to said first discriminator and exhibiting a delay greater than or equal to the maximum signal delay through said helical coil;
   a time-to-amplitude converter (TAC) coupled to said delay line means and said second threshold level discriminator; and
   a pulsed height analyzer coupled to said time to amplitude converter.

9. A system according to claims 1, 2, 3, 4, 5, 6 or 7 or 8 further comprising:
   said ionizable gas consisting of 70% Ar, 29% Isobutane, 0.6% Freon, 13Bi, and 0.4% methylal.

* * * * *